United States Patent [19]

Kershaw

[11] 4,042,629

[45] Aug. 16, 1977

[54] PREPARATION OF HEXAMETHYLENE DIAMINE FROM 2-CYANOCYCLOPENTANONE AND ADIPONITRILE

[75] Inventor: Bernard John Kershaw, Kingston, Canada

[73] Assignee: Du Pont of Canada, Montreal, Canada

[21] Appl. No.: 693,115

[22] Filed: June 4, 1976

[51] Int. Cl.$^2$ ............................................. C07C 87/14
[52] U.S. Cl. .............................. 260/583 P; 260/465.4; 260/583 K; 260/583 L
[58] Field of Search .......... 260/583 K, 585 C, 583 P, 260/583 L, 570.8 TC, 563 R

[56] References Cited

U.S. PATENT DOCUMENTS 3,696,153  10/1972   Kershaw et al. ..................... 252/459

OTHER PUBLICATIONS

Best et al., "J. Chem. Soc.", vol. 95, pp. 685–714 (1909).
Astle, "Industrial Organic Nitrogen Compounds", pp. 24 and 25 (1961).

Primary Examiner—Daniel E. Wyman
Assistant Examiner—John J. Doll

[57] ABSTRACT

Process for the manufacture of hexamethylene diamine comprising the steps of contacting 2-cyanocyclopentanone alone or in mixture with adiponitrile with a mixture comprising ammonia and hydrogen in the presence of a catalyst prepared by reducing iron oxide with hydrogen. The process is conveniently conducted at a temperature in the range 100° to 275° C and at a pressure in the range of 300 to 600 kg/cm$^2$. The mole ratio of ammonia to 2-cyanocyclopentanone is maintained at least 4:1 and the pressure of hydrogen is sufficient to essentially prevent conversion of the activated catalyst to iron oxide.

8 Claims, No Drawings

PREPARATION OF HEXAMETHYLENE DIAMINE FROM 2-CYANOCYCLOPENTANONE AND ADIPONITRILE

BACKGROUND OF THE INVENTION

1. Field of the Invention

The present invention relates to a process for the manufacture of hexamethylene diamine, and in particular, to a process for the manufacture of hexamethylene diamine from 2-cyanocyclopentanone, especially 2-cyanocyclopentanone mixed with adiponitrile.

2. Description of the Prior Art

Adiponitrile can be obtained by reacting adipic acid with ammonia in the presence of a dehydrating catalyst, for example, by the techniques disclosed in U.S. Pat. No. 2,200,734 to Arnold and Lazier issued on May 14, 1940 and in U.S. Pat. No. 2,273,633 to M. L. A. Fluchaire, issued on Feb. 17, 1942. The catalytic hydrogenation of dicyanobutene to adiponitrile is described in U.S. Pat. No. 2,532,311 to B. W. Howk and M. W. Farlow, issued on Dec. 5, 1950. Adiponitrile produced by these processes contains impurities, some of which boil at temperatures close to the boiling point of adiponitrile, e.g. 2-cyanocyclopentylideneimine. Impurities in the adiponitrile may lead to impurities in subsequent derivatives, in particular in hexamethylene diamine, that are difficult to remove. Failure to remove these latter impurities may result in inferior and variable properties, especially in polymers manufactured using such impure hexamethylene diamine.

Adiponitrile can be purified by the process disclosed in U.S. Pat. No. 3,879,436, issued on Apr. 22, 1975 to B. J. Kershaw and M. G. Pounder. 2-Cyanocyclopentylideneimine in adiponitrile, may also be hydrolyzed to 2-cyanocyclopentanone using a solid acidic catalyst in the presence of water and at a temperature of at least 140° C. The solid acidic catalysts may be silica-alumina catalysts, crystalline aluminosilicates, boron phosphate of titania-alumina as disclosed in U.S. Pat. No. 3,775,258 issued on Nov. 27, 1973 to B. J. Kershaw. The 2-cyanocyclopentanone is more easily separated from adiponitrile by techniques known in the art.

SUMMARY OF THE INVENTION

A process for the manufacture of hexamethylene diamine comprising contacting 2-cyanocyclopentanone with a mixture comprising ammonia and hydrogen in the presence of a catalyst selected from the group consisting essentially of promoted and unpromoted iron oxide, which catalyst has been activated by the reduction of said oxide, said process being conducted at a temperature in the range 100° to 275° C and at a pressure in the range of 300 to 600 kg/cm$^2$, wherein the mole ratio of ammonia to 2-cyanocyclopentanone is maintained at least 4:1 and the pressure of hydrogen is sufficient to prevent substantial conversion of the activated catalyst to iron oxide. More particularly, the reactants consist essentially of a mixture of adiponitrile and 2-cyanocyclopentanone containing 0.05 to 0.60% by weight of 2-cyanocyclopentanone and the process is conducted at a temperature in the range 100° to 200° C and at a pressure in the range of 300 to 600 kg/cm$^2$.

DETAILED DESCRIPTION OF THE INVENTION

The 2-cyanocyclopentanone can be obtained from a variety of sources, e.g. it can be purified 2-cyanocyclopentanone obtained commercially or as a component of a process stream in an impure state, e.g. the 2-cyanocyclopentanone can be a minor component in a stream of adiponitrile. However, it is important that any impurities present in the 2-cyanocyclopenanone do not significantly deactivate the catalyst.

The process is carried out at a temperature in the range of 100° to 275° C, preferably in the range 100° to 200° C when the 2-cyanocyclopentanone is admixed with adiponitrile. Lower temperatures are operable but not preferred because lower conversion rates can result. Temperatures above 275° C may result in losses of hexamethylene diamine especially as hexamethyleneimine.

The preferred pressure range is 300 to 600 kg/cm$^2$. Lower pressures favor the formation of incompletely hydrogenated compounds and secondary amines. Sufficient hydrogen pressure should be maintained to ensure that the activated iron catalysts are not converted to iron oxide, e.g. by water which is a by-product of the process of the present invention. Higher pressures are operable at an economic penalty.

The mole ratio of ammonia to 2-cyanocyclopentanone may be as high as about 270:1. Higher ratios can be used but may not be economically desirable. Undesirable byproducts such as secondary amines can be formed at mole ratios below the preferred ratio of at least 4:1.

Although it is preferred that the reaction pressure be attained through the use of hydrogen and ammonia, an inert gas, e.g. nitrogen, helium or argon, can be present as a minor component.

The preferred catalysts in the present process are activated iron oxide catalysts which can be unpromoted or promoted by acidic and/or basic metal oxide promoters. The preparation of such catalysts is described in Canadian Pat. No. 907,059 issued on Aug. 8, 1972 to J. R. B. Boocock, F. T. Flood and B. J. Kershaw. The use of such catalysts for the hydrogenation of adiponitrile is described in U.S. Pat. No. 3,696,153 issued on Oct. 3, 1972 to B. J. Kershaw, M. G. Pounder and K. R. Wilkins. The activation of such catalysts may be accomplished by heating the catalyst to 400° C in the presence of hydrogen or carbon monoxide.

The present process can be batch or continuous.

In one embodiment of the process of the present invention the 2-cyanocyclopentanone is obtained in mixture with adiponitrile and is present at a concentration of 0.05 to 0.60% by weight based upon the weight of the mixture and preferably 0.10 to 0.50% by weight on the same basis.

In a particularly preferred embodiment the process of the present invention is used in the manufacture of hexamethylene diamine from adiponitrile and especially from adiponitrile manufactured by the reaction of adipic acid and ammonia. Adiponitrile obtained by reacting adipic acid and ammonia usually contains 2-cyanocyclopentylideneimine. Prior to converting the adiponitrile to hexamethylene diamine, the 2-cyanocyclopentylideneimine is converted to 2-cyanocyclopentanone using, for example, the process described in Canadian Pat. No. 912,036. In the absence of steps to concentrate the 2-cyanocyclopentanone in the adiponitrile or to purify the adiponitrile by separating 2-cyanocyclopentanone from the adiponitrile, the amount of 2-cyanocyclopentanone in the adiponitrile will usually be in the range of 0.05 to 0.60% by weight and can be contacted with the activated catalyst under the conditions described hereinbefore, thereby economically converting both the adiponitrile and the 2-cyanocyclopentanone into hexamethylene diamine.

The following examples are presented to illustrate, but not to restrict, the present invention. Parts and percentages are by weight unless otherwise indicated.

EXAMPLE 1

The conversion of 2-cyanocyclopentanone to hexamethylene diamine was carried out in two experiments in a 100 ml, high pressure stainless steel autoclave. The amount and type of catalyst shown in Table I along with 1.5 grams of 2-cyanocyclopentanone were placed in the autoclave which had been purged with nitrogen. Approximately 32 ml of anhydrous ammonia were added followed by hydrogen until a pressure of about 110 kg/cm$^2$ was obtained. The temperature of the contents of the autoclave was raised to the indicated temperature and maintained at that temperature for 90 minutes following which the autoclave was allowed to cool to room temperature before being vented through a series of traps containing methanol and a trap cooled by ice. The trap and autoclave contents were analyzed by gas-liquid chromatography. The results are reported in Table I.

TABLE I

| | Run A*** | Run B |
|---|---|---|
| Catalyst No.* | I | II |
| Catalyst weight (gm) | 1.9 | 2.0 |
| Reaction temperature (° C) | 252–260 | 256–259 |
| Reaction pressure (kg/cm$^2$) | 480–520 | 470–485 |
| Yield (%)** | | |
| Hexamethylene diamine | 54 | 66 |
| Hexamethyleneimine | 16 | 17 |
| Caprolactam | 0 | 5 |
| Cyclopentylamine | 30 | 6 |
| N-hexylamine | 0 | 2 |
| 2-(aminomethyl)cyclopentylamine | — | — |

*Catalyst I was alumina promoted iron oxide activated by reduction with hydrogen at 400° C. Catalyst II was ferric oxide activated at 325° C for 18 hours in the presence of carbon monoxide.
**Mole percent based on moles of 2-cyanocyclopentanone charged.
***Analysis done on sample which accounted for only 67% of 2-cyanocyclopentanone charged.

EXAMPLE 2

Adiponitrile containing 10% 2-cyanocyclopentanone was mixed with ammonia and hydrogen and fed at the rates shown in Table II and at a pressure of 350 kg/cm$^2$, to a continuous stainless steel tubular reactor containing 380 grams of catalyst. The reactor measured approximately 14 inches in length by one inch in diameter. The catalyst was 8/14 mesh iron oxide containing the promoters Al$_2$O$_3$— K$_2$O—CaO that had been activated by reduction with 55–60 scfh of hydrogen at 400° C for 65 hours at which time the catalyst was 91% reduced. The products of the reaction were analyzed by gas-liquid chromatography. The results are reported in Table II.

TABLE II

| | Run A | Run B |
|---|---|---|
| 2-Cyanocyclopentanone (gm/hr) (in adiponitrile) | 44 | 62 |
| Ammonia (gm/hr) | 1810 | 1870 |
| Hydrogen (1/hr) | 2290 | 2210 |
| Reactor temperature (inlet) ° C | 105 | 107 |
| (outlet) ° C | 155 | 148 |
| Yield (%)* | | |
| Hexamethylene diamine | 55 | 54 |
| Caprolactam | 5 | 9 |
| 2-(aminomethyl)cyclopentylamine | 8 | 4 |
| Unidentified low boiling point fraction (approx. 138° C) | 12 | 15 |
| Unidentified high boiling point fraction (approx. 234° C) | 20 | 18 |

*Moles percent based on the amount of 2-cyanocyclopentanone charged.

EXAMPLE 3

Adiponitrile, that has been manufactured from adipic acid ammonia and treated to convert 2-cyanocyclopentylideneimine to 2-cyanocyclopentanone, was continuously fed to a commercial scale reactor containing an iron catalyst. The iron catalyst was activated by reducing a naturally occurring iron oxide ore with hydrogen at about 400° C.

Four runs were conducted under the following conditions:

| Reaction Temperature (° C) | 110–120 |
|---|---|
| Pressure (kg/cm$^2$) | 315–364 |
| Ammonia (kg/kg of adiponitrile) | 4.0–4.5 |
| Hydrogen (1/hr per kg of adiponitrile) | 2600–3200 |

The results are reported in Table III.

TABLE III

| | Run A | Run B | Run C | Run D |
|---|---|---|---|---|
| Analysis of Adiponitrile | | | | |
| 2-Cyanocyclopentylidene-imine (ppm) | 1740 | 1950 | 940 | 1790 |
| 2-Cyanocyclopentanone (ppm) | 650 | 1200 | 3370 | 3820 |
| Analysis of Hexamethylene Diamine (No detectable ketone) | | | | |
| Hexamethyleneimine (ppm) | NA | NA | NA | 0.2 |
| 2-(aminomethyl)cyclopentyl-amine (ppm) | 1540 | 1480 | 1180 | 1670 |
| Under-conversion products (ppm) | <100 | <100 | <100 | <100 |

NA - not available

No adverse effects on the conversion of adiponitrile to hexamethylene diamine or on the hexamethylene diamine obtained when adiponitrile containing 2-cyanocyclopentanone was fed to the reactor. The amount of 2-(aminomethyl)cyclopentylamine in the hexamethylene diamine produced corresponded to the 2-cyanocyclopentylideneimine in the feed.

I claim:

1. A process for the manufacture of hexamethylene diamine comprising contacting 2-cyanocyclopentanone with a mixture comprising ammonia and hydrogen in the presence of a catalyst selected from the group consisting of promoted and unpromoted reduced iron oxide, at a temperature in the range 100° to 275° C and at a pressure in the range of 300 to 600 kg/cm$^2$, while maintaining the mole ratio of ammonia to 2-cyanocyclopentanone at at least 4:1 and providing sufficient hydrogen to prevent substantial conversion of the reduced catalyst to iron oxide.

2. The process of claim 1 in which the mole ratio of ammonia to 2-cyanocyclopentanone is in the range of about 4:1 to about 270:1.

3. The process of claim 2 in which the temperature is in the range 100° to 200° C.

4. The process of claim 3 in which adiponitrile is present along with the 2-cyanocyclopentanone.

5. A process for the manufacture of hexamethylene diamine comprising the steps of contacting a mixture consisting essentially of adiponitrile and 0.05 to 0.60% by weight based upon the weight of the mixture of 2-cyanocyclopentanone with a mixture comprising ammonia and hydrogen in the presence of a catalyst selected from the group consisting of promoted and unpromoted reduced iron oxide, at a temperature in the range 100° to 200° C and at a pressure in the range of 300 to 600 kg/cm$^2$, while maintaining the mole ratio of ammonia to 2-cyanocyclopentanone at at least 4:1 and providing sufficient hydrogen to prevent substantial conversion of the reduced catalyst to iron oxide.

6. The process of claim 5 in which the mole ratio of ammonia to 2-cyanocyclopentanone is in the range of about 4:1 to about 270:1.

7. The process of claim 6 in which the mixture of adiponitrile and 2-cyanocyclopentanone contains 0.10 to 0.50% by weight of 2-cyanocyclopentanone.

8. The process of claim 7 in which the adiponitrile is adiponitrile manufactured from adipic acid and ammonia.

* * * * *